(12) United States Patent
Alberts

(10) Patent No.: US 9,320,764 B2
(45) Date of Patent: Apr. 26, 2016

(54) METHOD FOR PRODUCING VITAMIN D IN A PERSON

(75) Inventor: David S. Alberts, Tucson, AZ (US)

(73) Assignee: TOPICAL TECHNOLOGIES, INC., Tucson, AZ (US)

( * ) Notice: Subject to any disclaimer, the term of this patent is extended or adjusted under 35 U.S.C. 154(b) by 1098 days.

(21) Appl. No.: 13/019,005

(22) Filed: Feb. 1, 2011

(65) Prior Publication Data

US 2011/0123469 A1  May 26, 2011

Related U.S. Application Data

(62) Division of application No. 12/397,904, filed on Mar. 4, 2009, now abandoned.

(51) Int. Cl.
| | |
|---|---|
| *A61K 35/60* | (2006.01) |
| *A61K 31/59* | (2006.01) |
| *A01N 43/16* | (2006.01) |
| *A61K 31/35* | (2006.01) |
| *A61K 33/06* | (2006.01) |

(52) U.S. Cl.
CPC ............... *A61K 35/60* (2013.01); *A61K 31/59* (2013.01)

(58) Field of Classification Search
CPC .................................................... A61K 33/60
USPC ........................................................ 514/167
See application file for complete search history.

(56) References Cited

U.S. PATENT DOCUMENTS

| | | |
|---|---|---|
| 5,256,417 A | 10/1993 | Koltisko |
| 5,387,798 A | 2/1995 | Funakoshi et al. |
| 5,422,099 A | 6/1995 | Holick et al. |
| 5,532,229 A | 7/1996 | Vieth |
| 6,696,049 B2 | 2/2004 | Vatter et al. |
| 6,734,440 B2 | 5/2004 | Questel et al. |
| 6,814,959 B1 | 11/2004 | Muller et al. |
| 7,371,396 B2 | 5/2008 | Ghisalberti |
| 2003/0152610 A1 | 8/2003 | Rolf et al. |
| 2006/0177390 A1 | 8/2006 | Person |

OTHER PUBLICATIONS

"Rethinking Sunscreen?" by Dr. Andrew Weil, Internet Web Posting, Nov. 7, 2005.
Web Page for Sunhealth Solutions, L.L.C., (www.sunhealthsolutions.com) as archived on Oct. 4, 2006.
Web Page for Springboard of Spring Valley, California (www.springboard4health.com/store/) as archived on Nov. 4, 2007 for Health Pro Lab ("HPL") brand topical vitamin D-3 cream.
"Measurement of solar ultraviolet radiation at a temperate and a topical site using polysulfone film", Davis et al., Polymer Degradation and Stability vol. 1, Issue 2, May 1979, pp. 121-132.

*Primary Examiner* — Layla Soroush

(74) *Attorney, Agent, or Firm* — Cahill Glaze PLC

(57) ABSTRACT

A method for enhancing production of Vitamin D within a person's skin includes a source of Vitamin D, a sunlight exposure indicator, and a sunscreen. Vitamin D, for example, cod liver oil, is applied to the skin topically via a patch or towlette, or ingested orally. The exposure indicator is worn by the user and changes its state to indicate that the person has been exposed to sunlight for a predetermined period of time. The user preferably waits a sufficient time for the Vitamin D to be absorbed into the skin, and then exposes his or her skin to direct sunlight, and monitors the exposure indicator to determine if it has changed state. The user applies the sunscreen to the user's skin after the exposure indicator changes state.

11 Claims, 2 Drawing Sheets

METHOD FOR PRODUCING VITAMIN D IN A PERSON

CROSS-REFERENCE TO RELATED APPLICATIONS

This patent application is a divisional application based upon co-pending U.S. patent application Ser. No. 12/397,904, filed Mar. 4, 2009, and the benefit of such earlier filing date is hereby claimed by Applicant under 35 U.S.C. §120.

BACKGROUND OF THE INVENTION

1. Field of the Invention

The present invention relates generally to Vitamin D production in the human body, and more particularly, to a method and related kit to facilitate the safe production of Vitamin D in the human body.

2. Description of the Related Art

Vitamin D includes Vitamin D-2 (ergocalciferol) and Vitamin D-3 (cholecalciferol). Vitamin D-3 is produced in human skin when it is exposed to ultraviolet B radiation present in sunlight. Vitamin D is known to regulate calcium and phosphorus levels in the blood. Vitamin D contributes to bone growth by helping bones absorb calcium. Lack of adequate Vitamin D can result in bone softening diseases, including rickets and osteomalacia. Osteomalacia, sometimes called "the adult form of rickets", causes a softening of the bones, joint pain, and a propensity for bone fractures. Even in the absence of osteomalacia, persons with inadequate Vitamin D intake may experience osteoporosis, also associated with joint pain, loss of bone density, and increased bone fragility.

Vitamin D, in adequate quantities, is also believed to exhibit anti-tumor activity. As D-3 is produced in the skin, it can regulate skin cell proliferation. Bodo Lehmann of the Department of Dermatology, Carl Gustav Carus Medical School, Dresden (Germany) University of Technology writes, " . . . mounting evidence indicates that cutaneous Vitamin D(3) synthesis is of high importance for the prevention of a broad variety of diseases, including various malignancies" (Photochemistry and Photobiology, volume 84, page 1246, 2005). Vitamin D supplementation may have a prominent role in cancer prevention as well as in the treatment of numerous forms of cancer, including skin, lung, breast, ovarian, gastrointestinal, colon and prostate cancers. For instance, recent epidemiological studies indicate that daily supplementation can markedly lower the risk of colon, breast and ovarian cancers. Therapeutically, it has been found that patients who receive chemotherapy or surgical treatment during the summer (i.e., have more sun exposure) have increased survival relative to patients treated in the winter. These data suggest that Vitamin D may contribute to patient survival. Furthermore, some Vitamin D-3 metabolites have themselves been used as chemotherapeutic agents with antiproliferative effects against several types of cancer including breast, colon, and prostate tumors, leukemias and lymphomas.

Vitamin D-3 is produced in the epidermal skin layer during sun exposure by conversion of 7-dehydrocholesterol. 7-Dehydrocholesterol, a cholesterol-like molecule present in the skin, is the precursor of Vitamin D-3 and forms cholecalciferol after being exposed to sunlight. Cholecalciferol (or "calciol") is the inactive, unhydroxylated form of Vitamin D-3. Cholecalciferol is thereafter hydroxylated in the liver to become calcidiol (25-hydroxyvitamin D-3). Calcidiol is further hydroxylated in the kidney to become calcitriol (1,25-dihydroxyvitamin D-3). Calcitriol is the active hormone form of Vitamin D-3.

While exposure to sunlight produces Vitamin D, over-exposure to sunlight poses its own risks, including skin cancer. People who live in warm, sunny climates have become so concerned about skin damage resulting from overexposure to ultraviolet radiation that many will not go outdoors without first applying sunscreen or wearing clothing that covers skin that would otherwise be exposed. As a result, it is now common for people who live in sunny, temperate locations to develop Vitamin D deficiencies. For example, a recent study has indicated that even persons residing in Southern Arizona commonly suffer from Vitamin D deficiency as a result of measures taken to avoid exposure to the ultraviolet rays of the sun. Those who avoid sun exposure altogether, or who extensively use sunscreen, prevent 25-hydroxyvitamin D in the skin from getting sufficient ultraviolet light (UVB) to be converted to 25-dihydroxyvitamin D, thereby leading to moderate to severe Vitamin D deficiency. As already explained, this can lead to severe osteoporosis, and increased rates of certain types of cancers.

It is believed that the adequate creation of Vitamin D requires only about ten to fifteen minutes of sun exposure per day to a person's skin without the protection of a sunscreen.

Topical application of Vitamin D to the skin is already known. For example, a topical cream form of cod liver oil is manufactured under the Health Pro Lab ("HPL") brand, and is available from Springboard of Spring Valley, Calif. Likewise, U.S. Pat. No. 5,422,099 (Holick, et al.), discloses pharmaceutical compositions of tachysterol and lumisterol for topical application to the skin in order to produce Vitamin D compounds in the skin when exposed to low energy sunlight.

Others have already described cosmetic compositions for topical application to the skin which include both a sunscreen as well as either cod liver oil or Vitamin D. For example, U.S. Pat. No. 6,696,049 (Vatter et al.) discloses a cosmetic composition that may include the oily ester emollient cod liver oil, as well as organic UV sunscreens. Likewise, in U.S. Pat. No. 7,371,396 (Ghisalberti), a dermatological composition is disclosed which includes Vitamin D (described as an active agent that modulates cutaneous pigmentation and/or proliferation and/or differentiation), as well as UV filters. U.S. Patent Application Publication No. US 2006/0177390 (Person), published on Aug. 10, 2006, discloses that increased use of sunscreens may be increasing certain cancer risks by preventing the skin from producing Vitamin D. The published Person application discloses the addition of Vitamin D to a topical sunscreen composition. Similarly, in U.S. Pat. No. 6,814,959 (Muller, et al.), a UV blocking agent is disclosed, and in one embodiment, cod liver oil is added. The problem, however, is that the combination of Vitamin D in the same carrier as the sunscreen will necessarily prevent the Vitamin D to be absorbed into the skin before the sunscreen begins blocking out the sun's UVB rays.

Still others have suggested the possibility of deferring the application of sunscreen, when going outdoors, for the purpose of enhancing Vitamin D production in the body. For example, in a Nov. 7, 2005 internet web posting entitled "Rethinking Sunscreen?", Dr. Andrew Weil answered a question asking whether constant use of sunscreen prevents the body from getting enough Vitamin D. In response, Dr. Weil stated that new findings have led some researchers to suggest that "we may have gone overboard by insisting that everyone wear sunscreen whenever in the sun", and suggested that "it may do you more good than harm to get out in the sun for 15 minutes or so without protection several days a week", and further suggesting that "[a]fterwards, go back inside and slather on the sunscreen."

However, there does not appear to be available an effective and convenient method or apparatus to facilitate production of Vitamin D in the skin while protecting the user from skin damage that often results from overexposure to UVB rays of the sun.

Accordingly, it is an object of the present invention to prevent a deficiency of Vitamin D from developing in a human body without posing additional risks to the subject.

It is another object of the present invention to safely treat a deficiency of Vitamin D in a human body.

It is a further object of the present invention to provide an apparatus that facilitates production of Vitamin D in human skin while guarding against damaging exposure to UVB radiation from the sun.

It is a still further object of the present invention to provide such an apparatus that is reliable, effective and easy to use.

Yet another object of the present invention is to provide a method for enhancing production of Vitamin D within a person's skin while protecting the person from excessive exposure to ultraviolet rays of the sun.

These and other objects of the invention will become more apparent to those skilled in the art as the description of the present invention proceeds.

SUMMARY OF THE INVENTION

Briefly described, and in accordance with one preferred embodiment thereof, the present invention relates to a method for enhancing production of Vitamin D within a person's skin while protecting the person from excessive exposure to ultraviolet rays of the sun, the method including the steps of first administering Vitamin D to the person. This step of administering Vitamin D preferably includes the step of applying Vitamin D topically to the person's skin; alternatively, the Vitamin D may be administered orally to the person. The method also includes the steps of providing an exposure indicator that changes its state to indicate that the person has been exposed to sunlight for a predetermined period of time, and securing the exposure indicator to the user's person. In practicing such method, the person then exposes his or her skin to direct sunlight while monitoring the exposure indicator to determine if it has changed state. Upon noting that the indicator has changed state, the person then applies sunscreen to his or her skin to protect against overexposure to UVB radiation.

In the preferred embodiment, the step of applying Vitamin D topically includes the topical application of cod liver oil to the person's skin. Ideally, the Vitamin D is topically applied in the form of cholecalciferol (Vitamin D-3), although it may also be applied in the form of Vitamin D-2. Topical application of the Vitamin D may be made by securing a patch to the user's skin; the patch preferably includes an adhesive that secures the patch to the skin, as well as a supply of cod liver oil or other source of Vitamin D absorbed therein. The adhesive is preferably of a type that permits passage of the Vitamin D therethrough for absorption into the skin. Alternatively, topical application of the Vitamin D may be made by wiping the person's skin with a towlette saturated with cod liver oil or another source of Vitamin D.

In practicing the aforementioned method, the Vitamin D is topically applied to a portion of the user's skin to be exposed to the sun, for example, to at least one forearm of the person. In order to permit the Vitamin D to become absorbed within the user's skin prior to UVB exposure, the Vitamin D is preferably applied topically approximately fifteen to sixty minutes before exposing the person's skin to direct sunlight. The exposure indicator is preferably configured to change its state after being exposed to direct sunlight for a period ranging between approximately 8 minutes and 16 minutes.

Another aspect of the present invention relates to a kit for enhancing production of Vitamin D within a person's skin while protecting the person from excessive exposure to ultraviolet rays of the sun. The aforementioned kit includes 1) a source of Vitamin D; 2) an exposure indicator that changes its state to indicate exposure to sunlight for a predetermined period of time; and 3) a sunscreen for application to the person's skin after the indicator has changed state. In the preferred embodiment of the invention, the source of Vitamin D is designed for topical application, although, in an alternate embodiment, the source of Vitamin D is in liquid, pill, or capsule form for being ingested orally. The source of Vitamin D is preferably provided as either a topical adhesive patch that can be secured to the skin, or as a towlette saturated with the Vitamin D. In the preferred embodiment, the patch, or towlette, is saturated with cod liver oil.

The exposure indicator is preferably of the type which exhibits a color change upon being exposed to UVB rays of the sun for a predetermined period of time, corresponding approximately to the time required for the UVB rays of the sun to activate Vitamin D in the skin. The exposure indicator preferably includes an adhesive for allowing the exposure indicator to be secured to the user's skin, clothing, or a hat.

In the preferred embodiment, the sunscreen is saturated within a towlette for wiping on the person's skin after the exposure indicator changes state to protect the user's skin from over-exposure to UVB radiation. The sunscreen is preferably of the type that has an SPF rating of between 15 and 50, and ideally between 30 and 50.

DETAILED DESCRIPTION OF THE PREFERRED EMBODIMENTS

Figure 1:
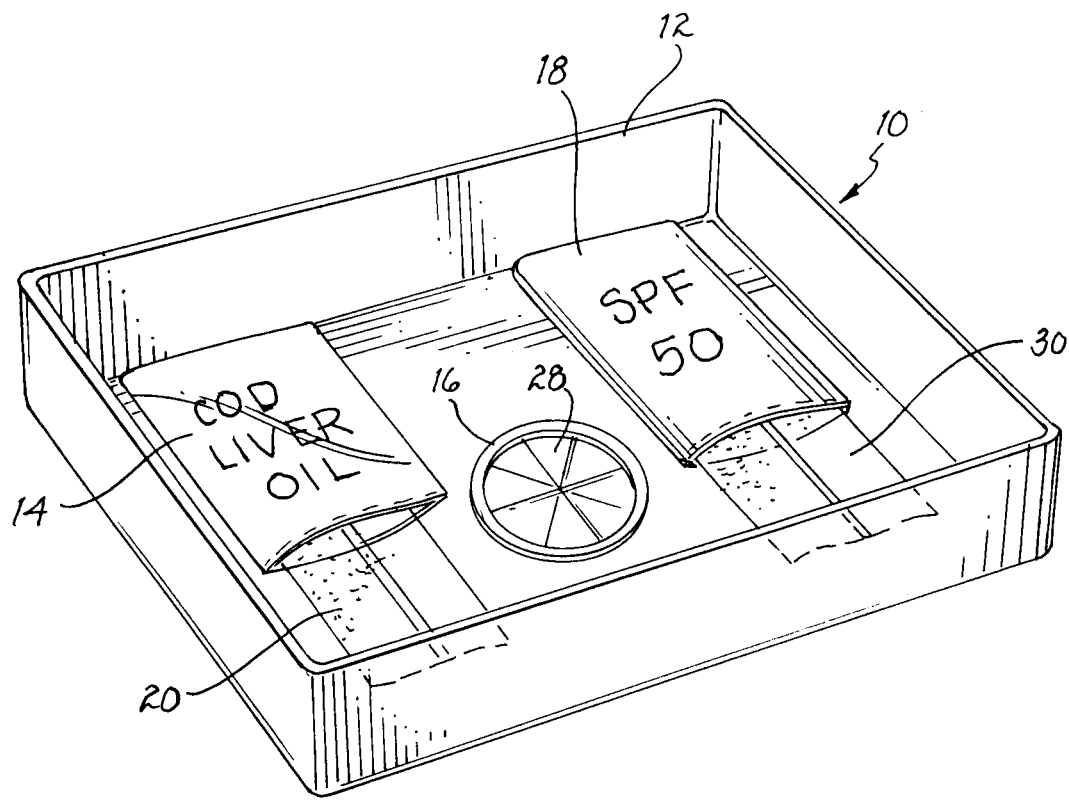
FIG. 1 is a perspective view of a packaged kit including a cod liver oil towlette, a UVB exposure indicator, and a sunscreen towlette.

A kit 10 is shown in FIG. 1 in accordance with a preferred embodiment of the present invention. Kit 10 may include an outer package or box 12 for containing the component parts of the kit. Within box 12 are a 1) a packet 14 of Vitamin D; 2) a UVB exposure indicator 16 that changes its state to indicate exposure to sunlight for a predetermined period of time; and 3) a packet of sunscreen to be applied to exposed portions of the user's skin after the indicator has changed state. Having all of the required items in a single-use, disposable kit encourages users to regularly apply Vitamin D for exposure to the sun without risking over-exposure to damaging UVB rays of sunlight.

As indicated in FIG. 1, packet 14 may be provided in the form of a tear-apart sealed foil envelope containing a towlette 20 saturated with cod liver oil for topical application to the user's skin. Towlette 20 can be removed from foil packet 14 and wiped across the portion of the user's skin that will be exposed to sunlight. As noted above, cod liver oil is a common source of Vitamin D-3 that is absorbed into the skin relatively easily. If desired, oral administration of dietary Vitamin D may be used as an alternative to direct topical application to the skin; in this case, packet 14 may contain a source of Vitamin D in liquid, pill or capsule form for being ingested by the user. However, topical application of Vitamin D is preferred. When Vitamin D is administered orally, the amount of Vitamin D which is actually present in exposed skin is not known, and the amount of time required for such Vitamin D to reach exposed areas of the skin is not readily determined.

Cod liver oil is a preferred form of Vitamin D for topical application to the skin. Cod liver oil includes Vitamin D in a fat-soluble form that can easily pass through the skin. Cod liver oil is considered to be a "cosmaceutical", is available for "over-the-counter" purchase, and its use does not require approval by the Food and Drug Administration (FDA)). Preferably, the cod liver oil is applied to portions of the skin that will be exposed to the sun approximately 15-30 minutes before sun exposure begins, as this period of time is usually sufficient for the Vitamin D to be absorbed through the skin. Ideally, the cod liver oil is applied to the posterolateral forearms 30 minutes before sun exposure.

Figure 2:
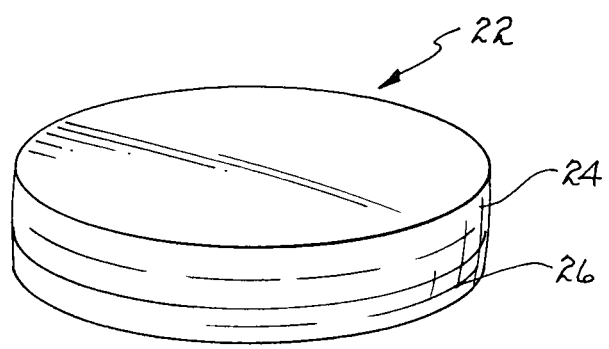
FIG. 2 is a perspective view of a patch serving as a source of Vitamin D.

Referring briefly to FIG. 2, towlette 20 may be replaced by a topical, transdermal skin patch 22. Skin patch 22 includes an upper substrate layer 24 saturated with a source of Vitamin D, such as cod liver oil. Below substrate layer 24 is an adhesive layer 26. Suitable adhesive patches are commercially available from the Medical/Pharmaceutical Division of Pacific Die Cut Industries of Hayward, Calif. Adhesive layer 26 may, for example, be a silicone pressure-sensitive adhesive commercially available from Dow Corning Corporation. In articular, Dow Corning supplies BIO-PSA® brand silicone pressure sensitive adhesives for transdermal and topical drug delivery. Such PSAs can be formulated to provide various rates of permeability, allowing for a controlled rate of delivery of cod liver oil (or other Vitamin D source) to the skin.

Such a transdermal skin patch could contain a single daily dose of Vitamin D and be thrown away after use each day. On the other hand, a longer-lasting patch, containing a week's supply, or even a month's supply, of Vitamin D, could also be provided, for being worn continuously by a user over a period of a week or month, respectively.

Whether the Vitamin D source is applied topically using a towlette or a patch, the Vitamin D is preferably applied to a portion of the user's skin that will be exposed to sunlight, for example, the user's forearms, or forehead. Following initial application of the patch 22 or towlette 20, the user preferably waits between 15-60 minutes before going outdoors so that the applied Vitamin D has sufficient time to be absorbed into the skin.

Before going outdoors, the user applies UVB exposure indicator 16 directly to the user's skin, or alternatively, to the user's clothing, or perhaps the user's hat. Indicator 16 includes an adhesive backing for such purpose. Indicator 16 also includes an upper face 28 which undergoes a change in color as UVB radiation strikes indicator 16. The preferred exposure indicator for use in practicing the invention is one commercially available from SunHealth Solutions, LLC of Naples, Florida under the product name "SunSignals UV Sensors". These exposure indicators are circular, self-adhesive, water-resistant, disposable, single-use patches, and change color as they react to UVB radiation. These sensors initially have a yellow color and turn orange after exposure to UVB radiation. One example of a sunlight dosage indicator is disclosed within U.S. Pat. No. 6,734,440 (Questel, et al.), the disclosure of which is hereby incorporated by reference. In the Questel '440 patent, the sensitivity of the indicator can be adjusted by controlling UV absorbing materials overlying the indicator layer. Exposure indicator 16 is configured to undergo a color change when it has received approximately 16-15 minutes (preferably 10-15 minutes) of mid-day direct sunlight, which is usually a sufficient amount of time to activate Vitamin D-3 in exposed skin.

After applying exposure indicator 16, the user goes outdoors for exposing the treated skin to direct sunlight. Following sufficient exposure, as signaled by the change in color of the exposure indicator, the user retrieves foil packet 18 from kit 10, and removes towlette 30 therefrom. Towlette 30 is saturated with a sunscreen having an SPF rating of between 15 and 50 (an SPF rating of 30-50 is preferred). The user then wipes towlette 30 across exposed portions of the user's skin to protect from further UVB exposure. Alternatively, the user covers the skin with protective clothing, or goes back indoors.

Figure 3:
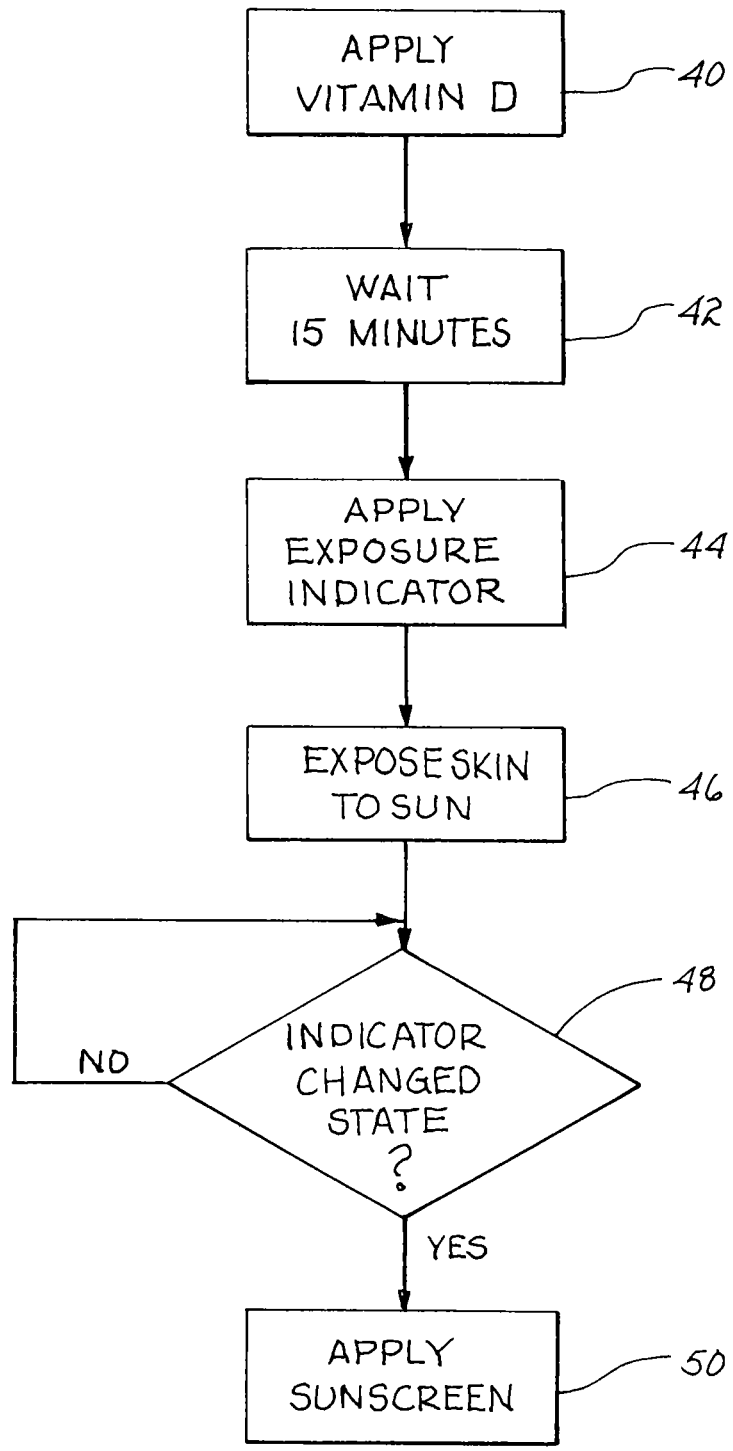
FIG. 3 is a flowchart showing the basic steps in practicing a preferred form of a method for producing Vitamin D in a person's skin.

Another aspect of the present invention relates to a method for enhancing production of Vitamin D within a person's skin while protecting the person from excessive exposure to ultraviolet rays of the sun. FIG. 3 illustrates a preferred embodiment of such a method in the form of a flowchart. In step 40, Vitamin D is first administered to the person. While the Vitamin D may be administered orally to the person, the preferred method is to apply the Vitamin D topically to a portion of the person's skin that will be briefly exposed to the sun, for example, to the person's forearm(s). In the preferred embodiment, Vitamin D in the form of cholecalciferol (Vitamin D-3), e.g., cod liver oil, is topically to the person's skin. However, Vitamin D-2 may also be topically applied to the person's skin. Such topical application may be accomplished, for example, by securing a patch to the user's skin, the patch having Vitamin D absorbed therein, or by wiping the person's skin with a towlette saturated with Vitamin D.

Still referring to FIG. 3, the person preferably waits at least 15 minutes after topical application of Vitamin D before exposing the person's skin to direct sunlight, as illustrated by step 42. While 15 minutes is usually a sufficient time for the Vitamin D to be absorbed into the skin, the Vitamin D is preferably applied approximately fifteen to sixty minutes before exposing the person's skin to direct sunlight.

When the person is ready to expose his or her forearm(s), or other portion of skin to which the Vitamin D has been applied, the person takes an exposure indicator and secures it to the person's skin, clothing, or a hat, as indicated by step 44 in FIG. 3. As noted above, the exposure indicator is designed to change its state to indicate that the person has been exposed to sunlight for a predetermined period of time, say, for example, for a period of approximately 8 minutes to 16 minutes. The person then exposes the portion of the person's skin to which the Vitamin D was topically applied to direct sunlight for exposure to UVB radiation, as indicated by step 46 in FIG. 3.

After exposing the skin to the sun, the person monitor's the exposure indicator to determine if it has changed state, as indicated by step 48 in FIG. 3. The person continues to monitor the state of the exposure indicator until it changes state. Upon detecting that the exposure indicator has changed state, the person applies sunscreen to exposed portions of the person's skin, as designated by step 50 in FIG. 3.

Those skilled in the art will now appreciate that an apparatus and method have been described to prevent and/or treat a deficiency of Vitamin D in a human body in a safe and reliable manner without posing additional risks of excessive UVB exposure to the subject. It will also be appreciated that the kit, and method, disclosed herein enhance Vitamin D production in a manner that is convenient and easy to use.

While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A method for enhancing production of Vitamin D within a person's skin while protecting the person from excessive exposure to ultraviolet rays of the sun, the method comprising the steps of:
   a) administering Vitamin D to the person;
   b) providing the person with an exposure indicator that changes its state to indicate that the person has been exposed to sunlight for a predetermined period of time;
   c) securing the exposure indicator to the user's person;
   d) exposing the person's skin and the exposure indicator to direct sunlight;
   e) monitoring the exposure indicator to determine if it has changed state; and
   f) applying sunscreen to the person's skin after the indicator has changed state; wherein the step of administering the Vitamin D includes the step of applying Vitamin D topically to the person's skin before step (d).

2. The method of claim 1 wherein the step of applying Vitamin D topically to the person's skin includes topical application of cod liver oil.

3. The method of claim 1 wherein the step of applying Vitamin D topically to the person's skin includes topical application of cholecalciferol (Vitamin D-3).

4. The method of claim 1 wherein the step of applying Vitamin D topically includes the step of securing a patch to the user's skin, the patch having Vitamin D absorbed therein.

5. The method of claim 1 wherein the step of applying Vitamin D topically includes the step of wiping the person's skin with a towlette saturated with Vitamin D.

6. The method of claim 1 wherein the step of applying Vitamin D topically includes the step of applying Vitamin D to at least one forearm of the person.

7. The method of claim 1 wherein the step of applying Vitamin D topically includes the step of applying Vitamin D approximately fifteen to sixty minutes before exposing the person's skin to direct sunlight.

8. The method of claim 7 wherein the exposure indicator changes its state after being exposed to direct sunlight for a period ranging between approximately 8 minutes and 16 minutes.

9. The method of claim 1 wherein the exposure indicator changes its state after being exposed to direct sunlight for a period ranging between approximately 8 minutes and 16 minutes.

10. The method of claim 1 wherein the step of administering Vitamin D to the person includes the step of administering Vitamin D approximately fifteen to sixty minutes before exposing the person's skin to direct sunlight.

11. The method of claim 10 wherein the exposure indicator changes its state after being exposed to direct sunlight for a period ranging between approximately 8 minutes and 16 minutes.

* * * * *